United States Patent [19]

Berger

[11] 4,137,251
[45] Jan. 30, 1979

[54] ANIONIC ARALIPHATIC COMPOUNDS

[75] Inventor: Alfred Berger, Reinach, Switzerland

[73] Assignee: Ciba-Geigy Corporation, Ardsley, N.Y.

[21] Appl. No.: 836,639

[22] Filed: Sep. 26, 1977

[30] Foreign Application Priority Data

Oct. 6, 1976 [LU] Luxembourg .............................. 75947
Feb. 16, 1977 [LU] Luxembourg .............................. 76778

[51] Int. Cl.² .................. C07C 141/14; C07C 141/16; D06P 3/24
[52] U.S. Cl. ...................................... 260/458 C; 8/173
[58] Field of Search ......................... 260/458 C, 458 R

[56] References Cited

U.S. PATENT DOCUMENTS

| | | | |
|---|---|---|---|
| 2,155,899 | 4/1939 | Harris | 260/458 R |
| 3,304,349 | 2/1967 | Shen | 260/458 R |
| 3,619,123 | 11/1971 | Walz et al. | 260/458 C |

Primary Examiner—Joseph E. Evans
Attorney, Agent, or Firm—Edward McC. Roberts; Prabodh I. Almaula

[57] ABSTRACT

Anionic araliphatic compounds which correspond to the general formula

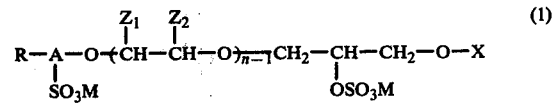

wherein
A is a mono- or binuclear aromatic radical,
R is alkyl having 4 to 22 carbon atoms,
X is alkyl having 1 to 18 carbon atoms, of $Z_1$ and $Z_2$, one is hydrogen and the other is hydrogen or methyl,
M is a cation, and n is 1 to 21; these compounds are particularly useful as dyeing auxiliaries, especially as levelling agents, in the dyeing or printing of synthetic polyamide fibres with anionic dyes.

8 Claims, No Drawings

ANIONIC ARALIPHATIC COMPOUNDS

The present invention relates to anionic araliphatic compounds, to a process for producing them, and to their use as dyeing auxiliaries for dyeing synthetic polyamide fibre material with anionic dyes.

The anionic araliphatic compounds according to the invention correspond to the general formula

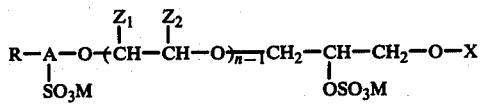

wherein
A is a mono- or binuclear aromatic radical,
R is alkyl having 4 to 22 carbon atoms,
X is alkyl having 1 to 18 carbon atoms, of $Z_1$ and $Z_2$, one is hydrogen and the other is hydrogen or methyl,
M is a cation, and n is 1 to 21.

A is preferably a benzene, naphthalene or diphenyl radical which is optionally further substituted. Possible substituents are, for example, hydroxyl, alkyl having 1 to 4 carbon atoms, alkoxy having 1 to 4 carbon atoms, or halogens such as chlorine. Preferably, A is a benzene radical, which can be further substituted with hydroxyl, chlorine, methyl or methoxy; but in particular A is an unsubstituted benzene radical.

The alkyl substituents R and X can be straight-chain or branched-chain. Examples of alkyl radicals are n-butyl, sec.-butyl, tert.-butyl, amyl, tert.-pentyl, n-hexyl, n-octyl, tert.-octyl, 2-ethylhexyl, nonyl, decyl, dodecyl, pentadecyl and octadecyl. X can also be methyl, ethyl, n-propyl or isopropyl, whilst R can also be eicosyl or docosyl.

$Z_1$ is preferably hydrogen, whilst $Z_2$ can be hydrogen and also methyl. In particular, $Z_1$ and $Z_2$ are both hydrogen.

As cation, M can be, for example, hydrogen, an alkali metal, especially sodium or potassium, an alkaline-earth metal, particularly magnesium or calcium, or an ammonium group. The term "ammonium group", in the context in which it is used here, relates both to ammonium ($NH_4^+$) and to substituted ammonium groups. The last-mentioned are derived, for example, from aliphatic amines such as di- or triethylamine, or mono-, di- or triethanolamine, from cycloaliphatic amines such as cyclohexylamine, or from heterocyclic amines such as piperidine, morpholine or pyridine. Preferably, M is hydrogen, an alkali metal or ammonium; and n is advantageously 1 to 6, preferably 1 to 3, and particularly 1.

For practical purposes, important anionic araliphatic compounds according to the present invention correspond to the general formula

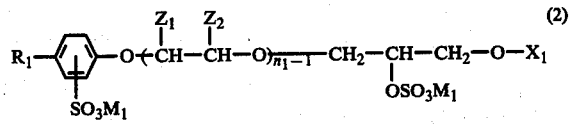

wherein
$R_1$ is alkyl having 4 to 18 carbon atoms, preferably 9 to 12 carbon atoms, of $Z_1$ and $Z_2$, one is hydrogen and the other is hydrogen or methyl, but both are preferably hydrogen, $X_1$ is alkyl having 1 to 8 carbon atoms, preferably 4 to 8 carbon atoms,
$M_1$ is hydrogen, alkali metal or an ammonium group, and
$n_1$ is 1 to 6, preferably 1 to 3.

As alkali metal, $M_1$ is particularly sodium or potassium; and as an ammonium group, it is especially ammonium or the trimethylammonium, monoethanolammonium, diethanolammonium or triethanolammonium group.

Of particular interest are anionic araliphatic compounds of the general formula

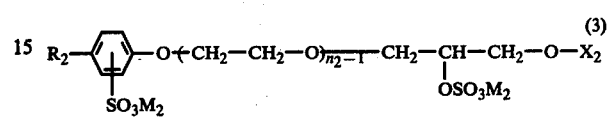

wherein
$R_2$ is alkyl having 9 to 12 carbon atoms,
$X_2$ is alkyl having 4 to 8 carbon atoms,
$M_2$ is hydrogen, alkali metal or ammonium, and
$n_2$ is 1 to 3, preferably 1.

The anionic araliphatic compounds according to the invention are produced by treating an araliphatic compound of the general formula

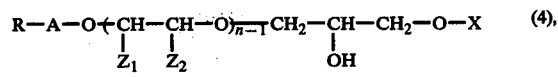

wherein A, R, X, $Z_1$, $Z_2$ and n have the given meanings, with a sulphonating agent; and optionally converting the sulphonation product into a salt.

The compounds of the formula (4), required as starting materials, are produced, for example, by reaction of a compound of the formula

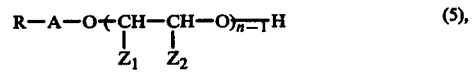

wherein A, R, $Z_1$, $Z_2$ and n have the given meanings, with a glycidyl ether compound of the formula

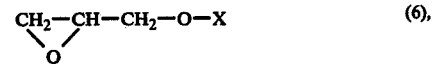

wherein X has the aforegiven meaning.

This reaction is performed preferably in the presence of an acid or alkaline catalyst, such as sodium, potassium, sodium hydroxide or potassium hydroxide, sodium methylate or potassium methylate or boron trifluoroetherate.

The treatment, according to the invention, of the starting materials of the formula (4) with the sulphonating agents is performed advantageously by customary methods, e.g. with concentrated sulphuric acid, sulphur trioxide or oleum, or preferably with chlorosulphonic acid. It is advantageously performed in a solvent inert under the reaction conditions. Suitable solvents are, for example, chlorinated hydrocarbons, such as chloroform, carbon tetrachloride, ethylene chloride, methylene chloride, trichloroethylene or trichloroethane; preferably however ethyl acetate, dimethylmethanephosphonate or diethylene glycol diethyl ether. The temperature range for the sulphonation is advantageously between 5° and 100° C., preferably between 50° and 70° C. The formed free acids can be subsequently converted into the corresponding alkali metal salts or ammonium salts. The conversion to the salts is effected in the usual manner by the addition of bases, such as ammonia, monoethanolamine, triethanolamine or preferably alkali metal hydroxides, for example sodium hydroxide or potassium hydroxide, at room temperature (20°–30° C.). There can be obtained in this manner aqueous preparations which contain, for example, 25 to 40% of the sulphonation product.

Depending on the size of the radicals R and X, and also on the operating conditions, there may be obtained cloudy preparations, which become however clear solutions when diluted with water. Eventual cloudy preparations can be converted into clear products also by the addition of an agent promoting solubility, such as in particular urea.

The new anionic araliphatic compounds are used as dyeing auxiliaries, especially as levelling agents, in the dyeing or printing of synthetic polyamide fibre material with anionic dyes. Suitable fibre materials are those made from adipic acid and hexamethylenediamine (polyamide 6.6), from ε-caprolactam (polyamide 6), from ω-aminoundecanoic acid (polyamide 11), from ω-aminoenanthic acid (polyamide 7), from ω-aminopelargonic acid (polyamide 8), or from sebacic acid and hexamethylenediamine (polyamide 6.10). The polyamide fibre materials can also be used as mixed fabrics, with each other or with other fabrics, for example mixtures of polyamide and wool or of polyamide and polyester. The fibre materials can be in the most varied stages of processing, e.g. in the form of flocks, looped fabric such as knitted goods or knitted fabrics, yarn, wound packages, non-woven fabrics or preferably fabrics.

In the case of the anionic dyes, these are, for example, salts of metal-free or heavy-metal-containing mono-, dis- or polyazo dyes, including the formazan dyes, as well as the anthraquinone, xanthene, nitro, triphenylmethane, naphthoquinoneimine and phthalocyanine dyes. Of interest also are the 1:1-and 1:2 metal-complex dyes. The anionic character of these dyes can be due to metal-complex formation and/or to acid, salt-forming substituents, such as carboxylic acid groups, sulphuric acid ester groups or phosphonic acid ester groups, phosphonic acid groups or sulphonic acid groups. These dyes can contain in the molecule also so-called reactive groupings, which form with the polyamide to be dyed a covalent bond. The dyes known as acid dyes are preferred.

The amount of dye to be added to the liquor is governed by the depth of colour desired; in general, amounts of 0.1 to 10 percent by weight, relative to the fibre material used, have proved satisfactory.

The dye baths can contain mineral acids such as sulphuric acid or phosphoric acid, organic acids, advantageously lower aliphatic carboxylic acids such as formic, acetic or oxalic acid, and/or salts such as ammonium acetate, ammonium sulphate or preferably sodium acetate. The acids serve principally to bring the liquors used according to the invention to the required pH value, which as a rule is 3.5 to 6.5, preferably 4 to 6. In addition, the dye baths can contain the customary electrolytes, dispersing agents, anti-foaming agents and wetting agents.

The dyeings are advantageously performed from an aqueous liquor using the exhaust process. The ratio of goods to liquor can accordingly be selected within a wide range, for example 1:1 to 1:100, preferably 1:10 to 1:50. The amounts in which the new anionic araliphatic compounds are added to the dye baths vary between 0.5 and 10 percent by weight, preferably 1 to 3 percent by weight, relative to the weight of the fibre material. Dyeing is expediently performed at a temperature within the range of 75° C. up to the boiling point, and preferably at a temperature of 90° to 98° C.

Preferably, the textile material is introduced into a liquor which has a temperature of 40° to 50° C., and the material is treated for 5 to 15 minutes at this temperature. The dyes are then added at 40° to 60° C., the temperature of the liquor is gradually raised, and dyeing is performed at the boiling temperature for 20 to 90 minutes, preferably for 30 to 60 minutes. The dye liquor is finally cooled, and the dyed material is rinsed and dried in the customary manner.

The dyeing of the synthetic polyamide fibre material can be carried out also by a printing process or padding process. The optionally thickened printing paste or the liquor, which contains the dye, the anionic araliphatic compound according to the invention, acid and eventual further additives, is printed or padded onto the fibre material, preferably at a temperature of between 10° C. and 40° C. The padded or printed fibre material is then subjected to a heat treatment, such as steaming, preferably at temperatures of 98° to 105° C. and at a pressure above atmospheric pressure, advantageously for 10 to 30 minutes.

The new anionic araliphatic compounds constitute valuable dyeing auxiliaries for dyeing synthetic polyamide fibre material. These materials can be evenly dyed with anionic dyes, especially with the "acid" dyes, with the avoidance of the material-induced streakiness which can occur, particularly in the case of polyamide fibre mixtures and fabrics.

Further advantages are the very small amount of foam formed by the dye baths containing the anionic araliphatic compounds according to the invention, the good water-solubility of these compounds and their good compatibility with other substances present in the dye bath, so that on dyeing at elevated temperature for a prolonged period of time there is no occurrence of undesirable precipitation or deposition on the fibre material. The products according to the invention have a stabilising effect on the dye baths, so that consequently these retain their full effectiveness throughout the entire dyeing operation.

In the following Examples, percentages are percent by weight and parts are parts by weight.

EXAMPLE 1

(a) 220 g of p-nonylphenol is stirred with 2 g of sodium hydroxide powder for 1 hour at 60–70° C. There is then added dropwise, within 45 minutes, 140 g of butyl glycidyl ether having an epoxy equivalent weight of 137 g; the mixture is heated to an external temperature of 120° C. and is maintained at this external temperature for 3 hours, with the internal temperature rising transiently to 145° C. To complete the reaction, the reaction mixture is subsequently held for 1 to 3 hours at 150–160° C.

(b) To 144 g of the intermediate product produced according to a) and 30 g. of ethyl acetate in a round-bottomed flask is added dropwise at 60° C., in the course of 2 hours, 106 g of chlorosulphonic acid. The sulphonation mixture is subsequently held for a further 2 hours at 60° C. The reaction mixture is then added at 20°-25° C., within 3 hours, to a mixture of 163 g of 30% sodium hydroxide solution and 120 g of water, and during this time the pH value of the solution is prevented from falling below 7-9 by the further addition of sodium hydroxide solution. The reaction product obtained is thereupon made up with water to a final weight of 630 g, with the resulting clear solution containing about 35% of the sulphonation product of the formula

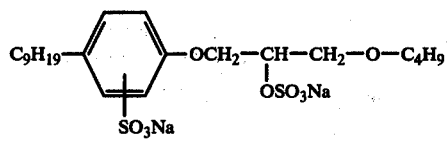

(11).

A 0.01% solution (relative to active substance) at 20° C. has a surface tension of 39.7 dyne/cm.

EXAMPLE 2

(a) 308 g of an adduct from 1 mole of p-nonylphenol and 2 moles of ethylene oxide is stirred with 2 g of sodium hydroxide powder for 1 hour at 60°-70° C. There is then added dropwise, within 45 minutes, 140 g of butyl glycidyl ether having an epoxy equivalent weight of 137 g; the mixture is heated to an external temperature of 120° C., and is maintained for 3 hours at this external temperature, whilst the internal temperature rises transiently to 132° C. To complete the reaction, the reaction mixture is subsequently held at 150°-160° C. for a further 1 to 3 hours.

(b) To 179.2 of the intermediate product produced according to a) and 30 g of ethyl acetate in a round-bottomed flask is added dropwise at 60° C., during 2 hours, 106 g of chlorosulphonic acid. The resulting sulphonation product is added, in the manner described in Example 1b), to 163 g of 30% sodium hydroxide solution and 120 g of water. The solution obtained is thereupon made up with water to a final weight of 724 g. There is obtained a clear solution containing about 35% of the sulphonation product of the formula

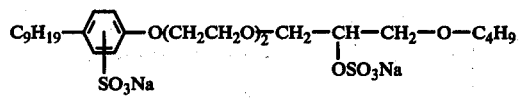

(12).

Surface tension at 20° C. = 37.5 dyne/cm, measured on a 0.01% solution (relative to active substance).

EXAMPLE 3

(a) 256 g of p-dodecylphenol is stirred with 2 g of sodium hydroxide powder for 1 hour at 60°-70° C. There is then added dropwise, within 45 minutes, 108 g of ethyl glycidyl ether having an epoxy equivalent weight of 105 g; the mixture is heated to an external temperature of 120° C., and is held for 3 hours at this temperature, whilst the internal temperature rises transiently to 150° C. The reaction is completed by holding the reaction mixture at 150°-160° C. for a further 1 to 3 hours.

(b) To 145.6 g of the intermediate product obtained according to a) and 30 g of ethyl acetate in a round-bottomed flask is added dropwise at 60° C., during 2 hours, 106 g of chlorosulphonic acid. The resulting sulphonation mixture is added, in the manner described in Example 1b), to 163 g of 60% sodium hydroxide solution and 120 g of water. The solution obtained is thereupon made up with water to a final weight of 632 g. There is obtained a clear solution which contains about 35% of the sulphonation product of the formula

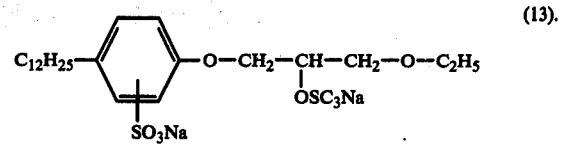

(13).

Surface tension at 20° C. = 40.7 dyne/cm, measured on a 0.01% solution (relative to active substance).

EXAMPLE 4

(a) 150 g of p-tert.-butylphenol is stirred with 2 g of sodium hydroxide powder for 1 hour at 60°-70° C. There is then added dropwise, within 45 minutes, 140 g of butyl glycidyl ether having an epoxy equivalent weight of 137 g; the mixture is heated to an external temperature of 120° C., and is held for 3 hours at this external temperature. The internal temperature rises transiently to 136° C. To complete the reaction, the reaction mixture is maintained at 150°-160° C. for a further 1 to 3 hours.

(b) To 116 g of the intermediate product produced according to a) and 30 g of ethyl acetate in a round-bottomed flask is added dropwise at 60° C., during 2 hours, 106 g of chlorosulphonic acid. The resulting sulphonation mixture is added, in the manner described in Example 1b), to 163 g of 30% sodium hydroxide solution and 120 g of water; and the solution obtained is then made up with water to a final weight of 602 g. A clear solution containing about 30% of the sulphonation product of the formula

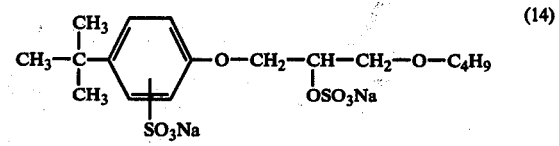

(14)

is obtained. A 0.01% solution (relative to active substance) has a surface tension of 54.5 dyne/cm at 20° C.

EXAMPLE 5

(a) 220 g of p-nonylphenol is stirred with 2 g of sodium hydroxide powder for 1 hour at 60°-60° C. There is then added dropwise, within 45 minutes, 200 g of 2-ethylhexyl glycidyl ether having an epoxy equivalent weight of 198 g; the mixture is heated to an external temperature of 120° C., and is held for 3 hours at this external temperature, whilst the internal temperature rises transiently to 133° C. To complete the reaction, the reaction mixture is then maintained at 150°-160° C. for a further 1 to 3 hours.

(b) To 168 g of the intermediate product produced according to a) and 30 g of ethyl acetate in a round-bottomed flask is added dropwise at 60° C., during 2 hours, 106 g of chlorosulphonic acid. The resulting sulphonation mixture is added, in the manner described in Example 1b), to 163 g of 30% sodium hydroxide solution and 120 g of water; and the product obtained is then made up with water to a final weight of 684 g. There is obtained a cloudy viscous preparation which readily dissolves in water and which contains about 35% of the sulphonation product of the formula

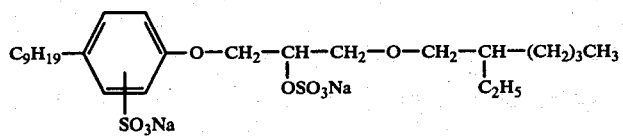

(15).

Surface tension at 20° C. is 35.7 dyne/cm, measured on a 0.01% solution (relative to active substance).

EXAMPLE 6

(a) 304 g of n-pentadecylphenol is stirred with 2 g of sodium hydroxide powder for 1 hour at 60°–70° C. There is then added dropwise, within 45 minutes, 126 g of isopropyl glycidyl ether having an epoxy equivalent weight of 123 g; the mixture is heated to an external temperature of 120° C., and is held for 3 hours at this external temperature, whilst the internal temperature rises transiently to 128° C. To complete the reaction, the reaction mixture is subsequently maintained at 150°–160° C. for 1 to 3 hours.

(b) To 172 g of the intermediate product produced according to a) and 30 g of ethyl acetate in a round-bottomed flask is added dropwise at 60° C., during 2 hours, 106 g of chlorosulphonic acid. The resulting sulphonation mixture is added, in the manner described in Example 1b), to 163 g of 30% sodium hydroxide solution and 120 g of water; and the product obtained is then made up with water to a final weight of 658 g. There is obtained a cloudy viscous product which readily dissolves in water and which contains about 35% of the sulphonation product of the formula

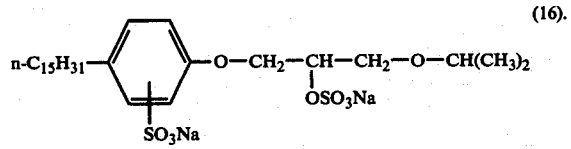

(16).

Surface tension at 20° C. is 51.1 dyne/cm, measured on a 0.01% solution (relative to active substance).

EXAMPLE 7

(a) 206 g of p-tert.-octylphenol is stirred with 2 g of sodium hydroxide powder for 1 hour at 60°–70° C. There is then added dropwise, within 45 minutes, 140 g of butyl glycidyl ether having an epoxy equivalent weight of 137 g; the mixture is heated to an external temperature of 120° C. and is held for 3 hours at this external temperature, whilst the internal temperature rises transiently to 125° C. To complete the reaction, the reaction mixture is subsequently maintained at 150°–160° C. for 1 to 3 hours.

(b) To 138.4 g of the intermediate product produced according to a) and 30 g of ethyl acetate in a round-bottomed flask is added dropwise at 60° C., in the course of 2 hours, 106 g of chlorosulphonic acid. The resulting sulphonation mixture is then added, in the manner described in Example 1b), to 163 g of 30% sodium hydroxide solution and 120 g of water; and the solution obtained in made up with water to a final weight of 596 g. A clear solution containing about 35% of the sulphonation product of the formula

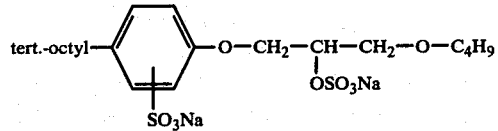

(17)

is obtained. The surface tension at 20° C. is 42.4 dyne/cm, measured on a 0.01% solution (relative to active substance).

EXAMPLE 8

(a) 220 g of p-nonylphenol is stirred with 2 g of sodium hydroxide powder for 1 hour at 60°–70° C. There is then added dropwise, within 45 minutes, 100 g of methyl glycidyl ether having an epoxy equivalent weight of 98 g; the mixture is heated to an external temperature of 120° C., and is held for 3 hours at this external temperature, whilst the internal temperature rises transiently to 136° C. The reaction is completed by maintaining the reaction mixture at 150°–160° C. for a further 1 to 3 hours.

(b) To 128 g of the intermediate product produced according to a) and 30 g of ethyl acetate in a round-bottomed flask is added dropwise at 60° C., in the course of 2 hours, 106 g of chlorosulphonic acid. The resulting sulphonation mixture is then added, in the manner described in Example 1b), to 163 g of 30% sodium hydroxide solution and 120 g of water, and the solution obtained is made up with water to a final weight of 547 g. A clear solution containing about 35% of the sulphonation product of the formula

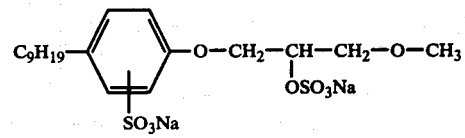

(18).

is obtained. The surface tension at 20° C. is 38.4 dyne/cm, measured on a 0.01% solution (relative to active substance).

EXAMPLE 9

72 g of the intermediate product produced according to Example 1a) and 50 ml of methylene chloride are placed into a round-bottomed flask. There is then added dropwise in the course of one hour at 5° C., with cooling, 49 g of chlorosulphonic acid; and the sulphonation mixture is stirred for 1 hour at 5°–10° C. and for 3 hours at 20°–30° C. It is subsequently heated to 60° C., whereupon the major amount of methylene chloride is distilled off. The reaction product is then neutralised with 27 g of monoethanolamine, in the process of which is formed a viscous mass, which is dissolved by the addition of 120 g of water. The product obtained is filtered, boiled, and made up with water to a final weight of 547 g. There is thus obtained a clear solution containing about 30% of the sulphonation product of the formula

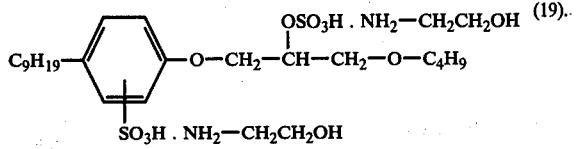

Surface tension at 20° C. is 42.3 dyne/cm, measured on a 0.01% solution (relative to active substance).

EXAMPLE 10

To 144 g of the intermediate product obtained according to Example 1a) and 30 g of ethyl acetate, in a round-bottomed flask, is added dropwise at 60° C., in the course of 2 hours, 94 g of chlorosulphonic acid. The resulting sulphonation mixture is added, in a manner similar to that described in Example 1b), to 147 g of 30% sodium hydroxide solution and 120 g of water, whereupon a cloudy product is obtained. The pH value of this is brought to 5 with acetic acid; and 60 g of urea is added to give a clear solution, which is then made up with water to a final weight of 630 g. The clear solution resulting contains about 35% of the sulphonation product. A 0.01% solution (relative to active substance) has a surface tension at 20° C. of 41.6 dyne/cm.

EXAMPLE 11

(a) 220 g of nonylphenol and 2 g of sodium methylate are heated to 140° C. There is then added dropwise in one hour, at an external temperature of 140° C., 140 g of butyl glycidyl ether having an epoxy equivalent weight of 137 g, and the internal temperature rises to about 150° C. The mixture is stirred for a further hour at an external temperature of 140° C., and subsequently maintained for 40 minutes at 155°-160° C.

(b) To 144 g of the intermediate product produced according to a) and 40 g of dimethylmethanephosphonate, in a round-bottomed flask, is added dropwise, in the course of 1-2 hours, 94 g of chlorosulphonic acid. The sulphonation mixture is thereupon held at 60° C. for a further 2 hours; the sulphonation product obtained is then added at 20°-25° C. within 3 hours to a mixture of 120 g of 30% ammonia and 155 g of water; and the resulting solution having a pH value of about 8 is subsequently made up with water to a final weight of 630 g. A clear solution containing about 35% of the compound of the formula

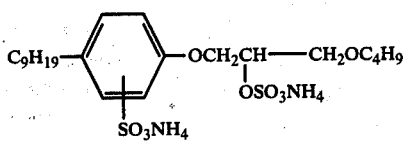

is obtained. The surface tension at 20° C. is 39.7 dyne/cm, measured on a 0.01% solution (relative to active substance).

EXAMPLE 12

(a) 220 g of the adduct from 1 mol of nonylphenol and 5 moles of ethylene oxide and 1 g of sodium methylate are heated to 140° C. There is added dropwise in 1 hour, at an external temperature of 140° C., 70 g of butyl glycidyl ether having an epoxy equivalent weight of 137 g. Stirring is maintained for 1 hour at 140° C., and the temperature is then held at 155°-160° C. for 2-3 hours.

(b) To 116 g of the intermediate product produced according to a) and 20 g of diethylene glycol diethyl ether is added dropwise during 1 hour at 60° C., in a round-bottomed flask, 53 g of chlorosulphonic acid, and the temperature is maintained at 60° C. for a further 2 hours. The reaction product obtained is then added in 3 hours at 20°-25° C. to a mixture of 60 g of ammonia (30%) and 80 g of water; and the resulting solution having a pH value of about 8 is thereupon made up with water to a final weight of 436 g. A clear solution containing about 35% of the compound of the formula

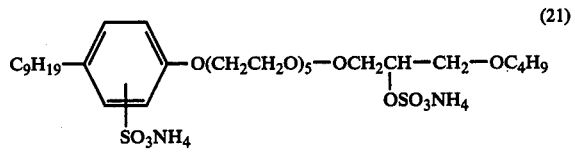

is obtained. The surface tension of the compound at 20° C. is 36.5 dyne/cm, measured on a 0.01% solution (relative to active substance).

EXAMPLE 13

(a) 308 g of the adduct from 1 mole of nonylphenol and 9 moles of ethylene oxide and 2 g of sodium methylate are heated to 140° C. There is then added dropwise, in one hour at an external temperature of 140° C., 70 g of butyl glycidyl ether having an epoxy equivalent weight of 137 g; stirring is maintained for a further hour at 140° C., and the temperature is then held at 155°-160° C. for 2-3 hours.

(b) To 151.2 g of the intermediate product produced according to (a) and 20 g of diethylene glycol diethyl ether in a round-bottomed flask is added dropwise at 60° C., in the course of 1½ hours, 53 g of chlorosulphonic acid, and the sulphonation mixture is held for a further 2 hours at 60° C. The reaction product is then added in 3 hours at 20°-25° C. to a mixture of 60 g of 30% ammonia and 80 g of water; and the solution obtained having a pH value of 8 is subsequently made up with water to a final weight of 542 g. A clear solution containing about 35% of the compound of the formula

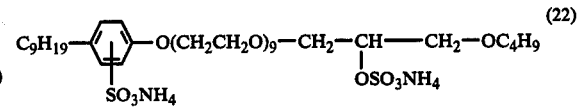

is obtained. The surface tension of the compound at 20° C. is 42.3 dyne/cm, measured on a 0.01% solution (relative to active substance).

EXAMPLE 14

(a) 275 g of the adduct from 1 mol of nonylphenol and 20 moles of ethylene oxide and 2 g of sodium methylate are heated to 140° C. There is then added dropwise in one hour, at an external temperature of 140° C., 35 g of butyl glycidyl ether having an epoxy equivalent weight of 137 g; stirring is maintained for a further hour at 140° C., and the temperature is then held at 155°-160° C. for 2-3 hours.

(b) To 124 g of the intermediate product produced according to (a) and 30 g of diethylene glycol diethyl ether in a round-bottomed flask is added dropwise at 60°

C., in the course of 1 hour, 27 g of chlorosulphonic acid, and the temperature is kept at 60° C. for a further 2 hours. The reaction product is then added within 3 hours at 20°-25° C. to a mixture of 30 g of 30% ammonia and 80 g of water. The solution obtained having a pH value of 8 is made up with water to a final weight of 406 g. A clear solution containing about 35% of the compound of the formula

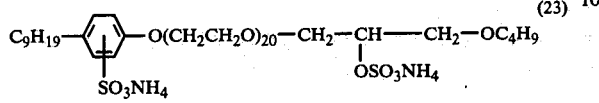
(23)

is obtained. The surface tension of the compound at 20° C. is 42.5 dyne/cm, measured on a 0.01 % solution (relative to active substance).

EXAMPLE 15

(a) 55.6 g of the adduct from 1 mole of nonylphenol and 1 mole of propylene oxide and 0.5 g of sodium methylate are heated to 140° C., whereupon there is added in 1 hour 28 g of butyl glycidyl ether having an epoxy equivalent weight of 137 g, in the process of which the temperature rises transiently to 145° C. The reaction mixture is subsequently held for 2 hours at 140° C. and for 2 hours at 150°-160° C. external temperature.

(b) To 62.7 g of the intermediate product produced according to (a) and 15 g of diethylene glycol diethyl ether in a round-bottomed flask is added dropwise at 60° C., in the course of 1 to 2 hours, 36 g of chlorosulphonic acid. The sulphonation mixture is then added within 3 hours at 20°-25° C. to a mixture of 45 g of 30% ammonia and 60 g of water, whereupon the resulting solution is made up with water to a final weight of 244 g. A clear solution which has a pH value of 8-9 and which contains about 35% of the compound of the formula

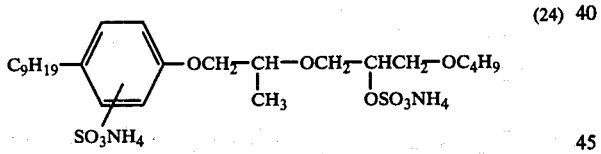
(24)

is obtained. The surface tension of a 0.01% solution (relative to active substance) at 20° C. is 34.8 dyne/cm.

EXAMPLE 16

(a) To 45.8 g of hexylnaphthol and 0.45 g of sodium methylate is added at 140° C., within 1 hour, 28 g of butyl glycidyl ether having an epoxy equivalent weight of 137 g, in the course of which the temperature rises transiently to 155° C. The external temperature is thereupon held for 2 hours at 140° C. and then for 2 hours at 150°-160° C.

(b) To 55.3 g of the intermediate product produced according to (a) is added dropwise, in a round-bottomed flask, 36 g of chlorosulphonic acid at 60° L C. in the course of 2 hours, whereupon the mixture is maintained at 60° C. for 2 hours. The sulphonation mixture is subsequently added in 3 hours at 20°-25° C. to a mixture of 45 g of 30% ammonia and 60 g of water; and the solution obtained is then made up with water to a final weight of 218 g.
A clear solution containing about 35% of the compound of the formula

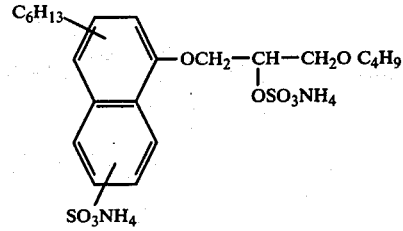
(25)

is obtained. The surface tension of a 0.01% solution (relative to active substance) at 20° C. is 38.9 dyne/cm.

EXAMPLE 17

(a) To 33 g of nonylphenol and 0.35 g of sodium methylate is added dropwise at 140° C., within 1 hour, 39.8 g of dodecyl glycidyl ether having an epoxy equivalent weight of 265 g, in the course of which the temperature rises transiently to 151° C. The external temperature is then held for 2 hours at 140° C. and for 2 hours at 150°-160° C.

(b) To 48.5 g of the intermediate product produced according to (a) and 20 g of diethylene glycol diethyl ether in a round-bottomed flask is added dropwise 24 g of chlorosulphonic acid, and the mixture is held for 2 hours at 60° C. The sulphonation mixture is subsequently added at 20°-25° C. during 3 hours to a mixture of 30 g of 30% ammonia and 40 g of water; and the mixture obtained is made up with water to a final weight of 181 g. There is obtained a thin paste which has a pH value of 8-9 and which contains about 35% of the compound of the formula

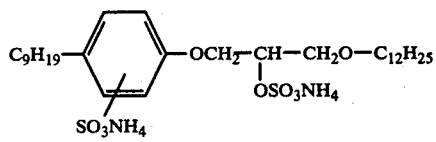
(26).

The surface tension of a 0.01% solution (relative to active substance) at 20° C. is 38.4 dyne/cm.

EXAMPLE 18

(a) 24.2 g of nonylphenol and 0.25 g of sodium methylate are heated to 60° C., and 41.8 g of stearyl glycidyl ether having an epoxy equivalent weight of 377 g is added. The mixture is then slowly heated to 140° C., and is held for 2 hours at this temperature and for 2 hours at 150°-160° C.

(b) To 60 g of the intermediate product produced according to (a) and 20 g of diethylene glycol diethyl ether in a round-bottomed flask is added dropwise at 60° C., in the course of 1-2 hours, 24 g of chlorosulphonic acid; and the temperature is kept at 60° C. for a further 2 hours. The sulphonation mixture is subsequently added at 20°-25° C. within 3 hours to a mixture of 30 g of 30% ammonia and 40 g of water; and the solution is then made up with water to a final weight of 202 g. A product containing about 35% of the compound of the formula (27)

$C_9H_{19}$—⬡—O—$CH_2$—CH—$CH_2$O $C_{18}H_{37}$
    |                    |
SO$_3$NH$_4$          OSO$_3$NH$_4$ is obtained. The surface tension of a 0.01% solution (relative to active substance) at 20° C. is 47.9 dyne/cm.

EXAMPLE 19

10 g of a barry dyeing polyamide 6.6 knitted fabric is treated for 10 minutes at 40° C. in 400 ml of a liquor which has been adjusted to pH 6 with 0.8 g of monosodium phosphate and 0.2 g of disodium phosphate, and which contains 0.1 g of the aqueous preparation produced according to Example 2. There are then added to the liquor 0.03 g of a dissolved commercial dye of the formula (101)

0.03 g of a dissolved commercial dye of the formula (102), and the knitted fabric is agitated for 10 minutes at 40° C. The dye liquor is then heated within 30 minutes to boiling temperature, and dyeing is performed for 60 minutes at this temperature. After the liquor has cooled, the dyed knitted fabric is rinsed with water and dried. A level green dyeing which is free from streakiness and which has good fastness properties is obtained.

Instead of using the preparation according to Example 2, it is also possible to use with similarly good results the aqueous preparations according to the Examples 1 and 3 to 18.

EXAMPLE 20

100 g of a streaky dyeing polyamide 6.6 knitted fabric is introduced into 4000 ml of a liquor which has been adjusted to pH 5 with 3.0 g of ammonium acetate and acetic acid, and which contains 2 g of the aqueous preparation produced according to Example 5. With continuous movement of the textile material, the bath temperature is raised within 25 minutes to 98° C. There is then added 0.5 g of a dissolved commercial dye of the formula (103), and dyeing is performed for 60 minutes at the boiling temperature. After the liquor has cooled, the dyed material is rinsed with water and dried. A level, brilliant violet dyeing which is free from streakiness and which has good fastness properties is obtained.

EXAMPLE 21

20 g of a streaky dyeing polyamide 6.6 knitted fabric is treated for 10 minutes at 40° C. in a bath which contains, dissolved in 800 ml of water, 0.4 g of the preparation produced according to Example 1, and which has been adjusted to pH 4 with 0.6 g of ammonium acetate and acetic acid. There is then added 0.1 g of a dissolved dye of the formula (103) given in Example 20, and stirring is maintained for a further 10 minutes at 40° C. The bath temperature is then raised within 30 minutes to 98° C. and dyeing is performed for 60 minutes at boiling temperature. After the liquor has been cooled, the dyed knitted fabric is rinsed with water and dried. A level, brilliant violet dyeing which is free from streakiness and which has good fastness properties is obtained.

Instead of using the preparation according to Example 1, it is possible to use, with similarly good results, also the aqueous preparations of the Examples 2 to 18.

I claim:

1. An anionic araliphatic compound of the general formula $$R-A-O-(CH-CH-O)_{n-1}CH_2-CH-CH_2-O-X \quad (1)$$
$$\qquad\quad |\quad\;\; |\qquad\qquad\qquad\qquad\;\; |$$
$$\qquad\quad Z_1\;\; Z_2\qquad\qquad\qquad\qquad OSO_3M$$
$$\;\;\; SO_3M$$

wherein
A is a mono- or binuclear aromatic radical,
R is alkyl having 4 to 22 carbon atoms,
X is alkyl having 1 to 18 carbon atoms, of $Z_1$ and $Z_2$, one is hydrogen and the other is hydrogen or methyl,
M is a cation, and n is 1 to 21.

2. A compound according to claim 1 wherein A is an unsubstituted or substituted benzene, diphenyl or naphthalene radical.

3. A compound according to claim 1 wherein A is an unsubstituted benzene radical or a benzene radical substituted by hydroxyl, chlorine, methyl or methoxy.

4. A compound according to claim 1 wherein M is hydrogen, alkali metal, alkaline-earth metal or an ammonium group.

5. A compound according to claim 1 wherein $Z_1$ is hydrogen and $Z_2$ is hydrogen or methyl.

6. A compound according to claim 1 wherein n is 1 to 6.

7. A compound according to claim 1 of the general formula

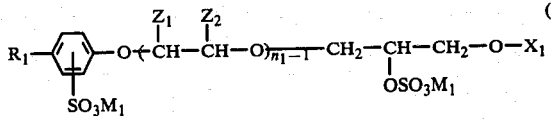 (2)

wherein
R₁ is alkyl having 4 to 18 carbon atoms, preferably 9 to 12 carbon atoms, of $Z_1$ and $Z_2$, one is hydrogen and the other is hydrogen or methyl, but both are preferably hydrogen,
$X_1$ is alkyl having 1 to 8 carbon atoms, preferably 4 to 8 carbon atoms,
$M_1$ is hydrogn, alkali metal or an ammonium group, and
$n_1$ is 1 to 6, preferably 1 to 3.

8. A compound according to claim 1 of the general formula

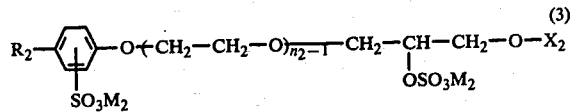 (3)

wherein
$R_2$ is alkyl having 9 to 12 carbon atoms,
$X_2$ is alkyl having 4 to 8 carbon atoms,
$M_2$ is hydrogen, alkali metal or ammonium, and $n_2$ is 1 to 3.

* * * * *